US00PP09616P

United States Patent [19]

Leue

[11] Patent Number: Plant 9,616

[45] Date of Patent: Jul. 30, 1996

[54] IMPATIENS PLANT NAMED 'PINK RUFFLE'

[75] Inventor: Ellen F. Leue, West Chicago, Ill.

[73] Assignee: Geo. J. Ball, Inc., West Chicago, Ill.

[21] Appl. No.: 446,555

[22] Filed: May 19, 1995

[51] Int. Cl.[6] ..... A01H 5/00

[52] U.S. Cl. ..... Plt./87.6

[58] Field of Search ..... Plt./87.6

*Primary Examiner*—Howard J. Locker

*Attorney, Agent, or Firm*—Burns, Doane, Swecker & Mathis

[57] ABSTRACT

A new and distinct cultivar of Impatiens plant, botanically known as *Impatiens wallerana,* and named 'Pink Ruffle' is provided. This new cultivar was the result of a controlled breeding program wherein a plant designated 359-2 (non-patented in the United States) was pollinated by a plant designated 30-2-2 (non-patented in the United States). The new cultivar is early blooming and forms in abundance attractive fully double coral-pink blooms. The foliage is medium green. The plant exhibits a good basal-branching character and exhibits an upright mounded growth habit. The new cultivar can be readily distinguished from the 'Rosebud Pink' cultivar (non-patented in the United States) in view of the more compact growth habit that is provided.

1 Drawing Sheet

SUMMARY OF THE INVENTION

The present invention provides a new and distinctive impatiens plant, botanically known as *Impatiens wallerana,* and hereinafter referred to by the cultivar name 'Pink Ruffle'.

The new cultivar is the product of a planned breeding program. More specifically, the breeding program which resulted in the production of the new cultivar was carried out in a controlled environment during June, 1991 at Elburn, Ill., U.S.A. The female parent (i.e., the seed parent) was a plant designated 359-2 (non-patented in the United States) which exhibits orange semi-double flowers and medium green foliage. The male parent (i.e., the pollen parent) was a plant designated 30-2-2 (non-patented in the United States) which exhibits orange double flowers with medium to deep green folaige. The parentage of the new cultivar can be summarized as follows:

359-2×30-2-2.

The seeds resulting from the above pollination were sown and plantlets were obtained which were physically and biologically different from each other. Selective study resulted in the identification of a single plant of the new cultivar. This plant had distinctive fully double coral-pink blooms and initially was designated 725-1.

It was found that the new cultivar of the present invention:

(a) exhibits attractive fully double coral-pink blooms in abundance,
(b) is early blooming,
(c) forms medium green foliage,
(d) exhibits a good basal-branching character, and
(e) exhibits an upright mounded growth habit.

Asexual reproduction of the new cultivar by stem cuttings taken during May and September, 1993, and during October, 1994, at Elburn, Ill., U.S.A., has demonstrated that the characteristics of the new cultivar as herein described are firmly fixed and are retained through successive generations of such asexual propagation.

The 'Pink Ruffle' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Rosebud Pink' cultivar (non-patented in the United States), it is found that the new cultivar exhibits a more compact growth habit (e.g., approximately 10.0 to 16.0 cm. in height×approximately 21.0 to 25.0 cm. in width vs. approximately 17.0×21.0 cm. in height ×approximately 22.0 to 27.0 cm. in width).

When plant material of the 'Pink Ruffle' cultivar is subjected to standard random amplified polymorphic DNA marker analysis (RAPD) using polymerase chain reaction (PCR) and a known unique set of DNA primers, it found to exhibit a different fingerprint map when compared to that of 'Rosebud Pink' cultivar which confirms its genetic distinctiveness.

Plants of the new cultivar will be marketed under the FIESTA trademark by Geo. J. Ball, Inc.

BRIEF DESCRIPTION OF THE PHOTOGRAPH

The accompanying photograph of FIG. 1 shows as true as it is reasonably possible to make the same in a color illustration of this type the general appearance of an overall plant of the new cultivar as seen primarily from above. The typical coral-pink blooms and foliage are illustrated. The plant was grown in a greenhouse at West Chicago, Ill., U.S.A.

DETAILED DESCRIPTION

Figure 1:
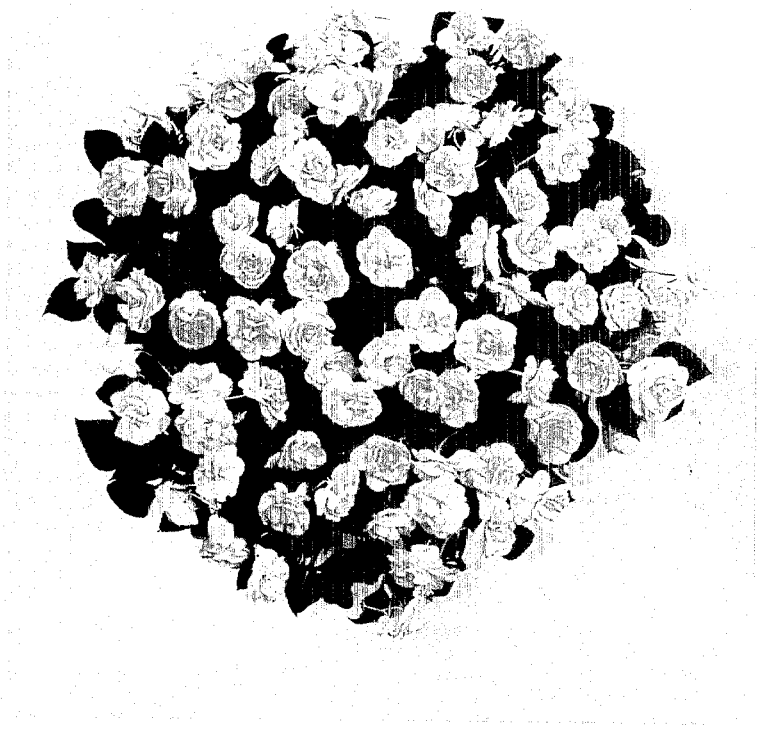

The chart used in the identification of colors described herein is the R.H.S. Colour Chart of The Royal Horticultural Society, London, England. The color values were determined on Jan. 3, 1995. The readings were taken between 10:00 and 11:00 a.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Two or three vegetative node stem cuttings from near the centers of the plants.

*Time to Initiate Roots.*—Approximately 7 to 14 days with the shorter times generally being experienced in the summer and the longer times in the winter.

*Rooting habit.*—Fibrous, and branching.

Plant description:

*Habit of growth.*—Basal-branching, and exhibits a medium upright mounded growth habit.

*Form.*—A mature plant at 8 weeks after the planting of a rooted cutting commonly measures approximately 10.0 to 16.0 cm. in height and approximately 21.0 to 25.0 cm. in width compared to approximately 17.0 to 21.0 cm. in height and approximately 22.0 to 27.0 cm. in width for the 'Rosebud Pink' cultivar.

*Foliage.*—The configuration is ovate with an acuminate tip. The leaves of the new cultivar commonly measure approximately 3.5 to 5.3 cm. in length and approximately 3.7 to 6.0 cm. in width while those of the 'Rosebud Pink' cultivar commonly measure approximately 5.5 to 6.0 cm. in length and approximately 3.7 to 4.0 cm. in width. The foliage is Green Group 137A (adaxial) and Yellow-Green Group 147B (abaxial) for both the 'Pink Ruffle' cultivar and the 'Rosebud pink' cultivar. The stem color is Yellow-Green Group 144B with streaks of Greyed-Purple Group 185A for both the 'Pink Ruffle' cultivar and the 'Rosebud Pink' cultivar.

Flower description:

*Flowering habit.*—Freely flowering. Small round buds become more oval with maturity and flowers open in a rose-like fashion.

*Natural flowering season.*—Early blooming and blooms throughout the year in a greenhouse environment.

*Flowers borne.*—Slightly above the foliage.

*Flower color.*—Red Group 55B on fully opened petals with the central area of tightly packed petals commonly being Red Group 55A (adaxial) and Red Group 55C (abaxial). This can be compared to Red Group 55D on fully opened petals with a central area of tightly packed petals of Red Group 55C (adaxial) and Red-Purple Group 62D (abaxial) for the 'Rosebud pink' cultivar.

*Quantity of flowers.*—Very floriferous. A mature plant commonly is totally covered with blooms.

*Number of petals.*—Fully double and petals commonly are too numerous to readily count.

*Petal shape.*—Round to oblong.

*Flower size.*—Approximately 3.6 to 4.0 cm. in diameter for the 'Pink Ruffle' cultivar and approximately 3.8 to 4.0 cm. in diameter for the 'Rosebud Pink' cultivar.

*Spur.*—One per flower of approximately 3.9 to 4.1 cm. in length and slightly curved which can be compared to one per flower of approximately 3.0 to 3.4 cm. in length with little or no curvature for the 'Rosebud Pink' cultivar.

*Spur color.*—Yellow-Green Group 145C for both the 'Pink Ruffle' cultivar and the 'Rosebud Pink' cultivar.

*Reproductive organs.*—The stamens are multiple in number and the styles and ovaries are generally typical of the species and non-distinctive.

I claim:

1. A new and distinct cultivar of *Impatiens wallerana* plant named 'Pink Ruffle' substantially as herein shown and described, which:

(a) exhibits attractive fully double coral-pink blooms in abundance,
(b) is early blooming,
(c) forms medium green foliage,
(d) exhibits a good basal-branching character, and
(e) exhibits an upright mounded growth habit.

* * * * *